United States Patent
Sperry (10) Patent No.: US 11,992,565 B2
(45) Date of Patent: May 28, 2024

(54) FOOD OR BEVERAGE CONTAINER SANITIZING SYSTEM

(71) Applicant: Sperry Product Innovation, Inc., Bedford, MA (US)

(72) Inventor: Laurence B. Sperry, Newton, MA (US)

(73) Assignee: Redi Technology, Inc., Bedford, MA (US)

( * ) Notice: Subject to any disclaimer, the term of this patent is extended or adjusted under 35 U.S.C. 154(b) by 408 days.

(21) Appl. No.: 17/201,666

(22) Filed: Mar. 15, 2021

(65) Prior Publication Data

US 2021/0308301 A1 Oct. 7, 2021

Related U.S. Application Data

(60) Provisional application No. 63/004,996, filed on Apr. 3, 2020.

(51) Int. Cl.
| | |
|---|---|
| *A61L 2/10* | (2006.01) |
| *A47L 15/00* | (2006.01) |
| *A47L 15/24* | (2006.01) |
| *A61L 2/26* | (2006.01) |

(52) U.S. Cl.
CPC ............ *A61L 2/10* (2013.01); *A47L 15/0065* (2013.01); *A47L 15/0071* (2013.01); *A47L 15/24* (2013.01); *A61L 2/26* (2013.01); *A61L 2202/11* (2013.01); *A61L 2202/122* (2013.01); *A61L 2202/23* (2013.01)

(58) Field of Classification Search
CPC ........................................................ A61L 2/10
See application file for complete search history.

(56) References Cited

U.S. PATENT DOCUMENTS

| | | | | |
|---|---|---|---|---|
| 5,606,759 | A | * | 3/1997 | Yang ...................... B08B 9/087 |
| | | | | 15/164 |
| 7,875,247 | B2 | | 1/2011 | Clark et al. |
| 8,747,770 | B2 | | 6/2014 | Davis |
| 9,289,523 | B2 | | 3/2016 | Lee |

(Continued)

FOREIGN PATENT DOCUMENTS

| | | |
|---|---|---|
| JP | 2009011878 | 1/2009 |
| KR | 2010-0007016 | 7/2010 |

(Continued)

OTHER PUBLICATIONS

<https://verilux.com/products/portable-sanitizing-wand>.

(Continued)

*Primary Examiner* — Eliza W Osenbaugh-Stewart
(74) *Attorney, Agent, or Firm* — Morse, Barnes-Brown & Pendleton, P.C.; Sean D. Detweiler, Esq.

(57) ABSTRACT

A sanitizing system for preventing the spread of harmful germs on food or beverage containers by utilizing a quick and compact UV sanitizing system. The doors of the pass-through chamber allow the customer to insert an un-sanitized container on the entry ("dirty") side of the system, and the retail employee to remove the sanitized container from the exit ("clean") side of the system without having to touch any other surface (doors, knobs, handles, etc.) than the container itself. The system utilizes movable UV light sources to minimize the time required for effective sanitizing.

15 Claims, 9 Drawing Sheets

(56) References Cited

U.S. PATENT DOCUMENTS

| | | | |
|---|---|---|---|
| 10,155,057 B2 | 12/2018 | Rizzone | |
| 2010/0012163 A1* | 1/2010 | Alpert | A47L 15/0089 |
| | | | 134/58 D |
| 2012/0223216 A1 | 9/2012 | Flaherty et al. | |
| 2013/0277574 A1* | 10/2013 | Dayton | A61L 2/10 |
| | | | 250/455.11 |
| 2014/0161663 A1 | 6/2014 | Farren et al. | |
| 2017/0057841 A1 | 3/2017 | Blood et al. | |
| 2017/0273534 A1* | 9/2017 | Alpert | A47L 15/4295 |
| 2018/0110890 A1* | 4/2018 | Matsui | A61L 2/10 |
| 2018/0361001 A1 | 12/2018 | Liao et al. | |
| 2019/0321504 A1 | 10/2019 | Dayton | |
| 2021/0282621 A1* | 9/2021 | Disch | A47L 15/0089 |
| 2022/0079413 A1* | 3/2022 | Longo | A47L 15/22 |
| 2023/0364284 A1 | 11/2023 | Sperry et al. | |

FOREIGN PATENT DOCUMENTS

| | | |
|---|---|---|
| KR | 2011-0099351 | 9/2011 |
| KR | 2013-0006786 | 11/2013 |
| KR | 10-1597453 | 2/2016 |
| KR | 2016-0098685 | 8/2016 |
| TW | 201918264 | 5/2019 |
| WO | WO 2015/012592 A1 | 1/2015 |
| WO | WO 2015/080768 A1 | 6/2015 |
| WO | WO 2016/054150 A1 | 4/2016 |
| WO | WO 2018/187681 A1 | 10/2018 |

OTHER PUBLICATIONS

<https://www.phonesoap.com/>.
<https://www.pro.phonesoap.com/>.
<https://www.steri-write.com/>.
<https://www.livelarq.com/>.

* cited by examiner

FOOD OR BEVERAGE CONTAINER SANITIZING SYSTEM

CROSS-REFERENCE TO RELATED APPLICATION(S)

This application claims priority to, and the benefit of, U.S. Provisional Application No. 63/004,996, filed Apr. 3, 2020, for all subject matter common to both applications. The disclosure of said provisional application is hereby incorporated by reference in its entirety.

FIELD OF THE INVENTION

The present invention relates to a sanitizing system suitable for sanitizing food or beverage containers. In particular, the present invention relates to an ultraviolet light based sanitizing system for food or beverage containers.

BACKGROUND

There is a growing trend of people bringing in their own reusable coffee cups or travel mugs to coffee shops. This trend has a very positive impact on reducing single-use cup waste. Unfortunately, this benefit can quickly be outweighed by the spread of germs (common cold, flu, norovirus, *E. coli*, coronavirus, etc.). The spreading of germs not only poses a public health threat, but it also dramatically increases waste through the treatment of the resulting sickness. In addition, even non-reusable containers, such as single use cups, can spread germs from server or barista to customer in the normal course of preparing food or a beverage in a container and serving it to a customer.

SUMMARY

There is a need for a small countertop proportioned system that quickly sanitizes food or beverage containers while making it convenient for both the customer and the retail employee to use. In order to minimize time required for sanitizing, the system automatically adjusts to each food or beverage container in terms of size, shape, overall dimensions, etc. This system eliminates the potential for customers spreading germs to retail employees (fewer sick days) and also eliminates the potential of the retail employee spreading customer's germs to all of the other customers by eliminating the handling of non-sanitized customer-handled containers.

In accordance with an embodiment of the present invention a food or beverage container sanitizing system is provided. The sanitizing system includes a housing, a chamber inside the housing, an access door providing access to the chamber, and at least one UV light source disposed within the chamber. The chamber is sized, dimensioned, and configured to envelope a food or beverage container. When the access door is in an open state it provides access to the chamber and when the access door is in a closed state it blocks access to the chamber. The at least one UV light source is configured to direct UV light at a predetermined intensity level and time duration onto a food or beverage container positioned inside the chamber in such a way as to result in sanitizing of surfaces of the food or beverage container. When the access door is in the closed state a UV sanitation cycle is initiated using the UV light source and when the UV sanitation cycle is complete, the access door is moved to the open state.

In accordance with aspects of the present invention, the sanitization system is designed and configured to accommodate reusable food or beverage containers. Such reusable food or beverage containers are designed to be washed or otherwise sanitized between uses. Alternately, the sanitizing system can be used with single use or disposable food or beverage containers.

In accordance with aspects of the present invention, the sanitizing system further includes a retrieval door opposite the access door, the retrieval door providing access to the chamber when the retrieval door is in an open state and blocking access to the chamber when the retrieval door is in a closed state. In some such aspects, the access door is configured to receive an un-sanitized food or beverage container and the retrieval door is configured to allow retrieval of a sanitized food or beverage container after the UV sanitation cycle. In further aspects, the sanitizing system includes a conveyor configured to receive an un-sanitized food or beverage container, move the container into the chamber through the access door, and move a sanitized container out of the chamber through the retrieval door. In some such aspects, the conveyor comprises a conveyor belt.

In accordance with aspects of the present invention, the sanitizing system further includes a container centering device disposed within the chamber. In some such aspects, the centering device comprises at least one mechanical arm.

In accordance with aspects of the present invention, the at least one UV light source comprises an array of UV lights. In some such aspects, an array of UV light is disposed on an inner surface of one or more sides of the chamber.

In accordance with aspects of the present invention, the at least one UV light source is disposed on a container profiler that is configured to conform to a shape of the container to place the at least one UV light source in proximity to an outer surface of the container allowing for effective sanitation at a lower intensity level or time duration. In some aspects, the profiler comprises one or more members having at least one UV light source mounted thereon, the members configured to move toward an outer surface of the container to place the UV light in proximity to the outer surface of the container. In some such aspects, the container profiler comprises a plurality of linear moving members. In other such aspects, the container profiler comprises articulating members. In further aspects, the profiler includes one or more sensors for detecting the shape of the container. In still other aspects, the container profiler is configured to rotate around the container to distribute application of UV light.

In accordance with aspects of the present invention, the sanitizing system further includes a rotating base for rotating a food or beverage container within the chamber.

In accordance with aspects of the present invention, the at least one UV light source is disposed on an arm that extends into an internal volume of the food or beverage container to sanitize an interior surface of the container. In some such aspects, the arm is configured to place the UV light source in proximity to the interior surface of the container allowing for effective sanitation at a lower intensity level or time duration. In still further aspects, the arm is configured to rotate within the internal volume of the container to distribute application of UV light.

In accordance with aspects of the present invention, the housing rotates around the chamber and wherein the access door, connected to the housing, receives un-sanitized food or beverage container in a first position located on a first side of the chamber and rotates to a second position located on second side of the chamber to provide access to a sanitized food or beverage container.

In accordance with aspects of the present invention, the sanitizing system further includes a second chamber inside the housing, a second access door, and at least one UV light source disposed within the second chamber. The second chamber inside the housing is sized, dimensioned, and configured to envelope a food or beverage container. The second access door provides access to the second chamber when the second access door is in an open state and blocks access to the second chamber when the second access door is in a closed state. The at least one UV light source is configured to direct UV light at a predetermined intensity level and time duration onto a food or beverage container positioned inside the second chamber in such a way as to result in sanitizing of surfaces of the food or beverage container. When the second access door is in the closed state a UV sanitation cycle is initiated using the UV light source and when the UV sanitation cycle is complete, the second access door is moved to the open state.

In accordance with aspects of the present invention, the access door is locked during the sanitation cycle and unlocked after the sanitation cycle is complete. In aspects with a retrieval door, the retrieval door is also locked during the sanitation cycle and unlocked after the sanitation cycle is completed.

In accordance with aspects of the present invention, the access door automatically transitions from a closed state to an open state to receive a food or beverage container. The automated transitioning can be in response to an activation signal provided by a button, switch or sensor. In certain aspects the automated transitioning is performed ins response to an RFID signal provided by an RFID tag provided in or on the food or beverage container. In aspects with a retrieval door, the retrieval door can be similarly automated.

In accordance with an embodiment of the present invention, a method for sanitizing a food or beverage container is provided. The method includes providing a sanitizing system as set forth herein, inserting an un-sanitized food or beverage container into the chamber, initiating a UV sanitation cycle sanitizing the food or beverage container, and retrieving the now sanitized food or beverage container from the chamber.

BRIEF DESCRIPTION OF THE FIGURES

These and other characteristics of the present invention will be more fully understood by reference to the following detailed description in conjunction with the attached drawings, in which.

DETAILED DESCRIPTION

Illustrative embodiments of the present invention relate to preventing the spread of harmful germs during the process of reusing cups by utilizing a quick and compact UV sanitizing system. The doors of a pass-through chamber of the system enable the customer to insert a used food or beverage container, such as a reusable food or beverage container, on the entry ("dirty") side of the system, and the retail employee to remove the sanitized food or beverage container from the exit ("clean") side of the system without having to touch any other surface (doors, knobs, handles, etc.) than the food or beverage container itself. The system utilizes movable UV light sources to minimize the time required for effective sanitizing.

FIG. 1A through FIG. 9, wherein like parts are designated by like reference numerals throughout, illustrate an example embodiment or embodiments of a food or beverage container sanitizing system that is sized, dimensioned, and configured as a countertop system or proportional equivalent, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

The sanitizing system 100 as seen in FIGS. 1A-9 comprises a housing 101, a chamber 102 inside the housing 101, an access door 103 providing access to the chamber 102, and at least one UV light source 106 disposed within the chamber 102. The chamber 102 is sized, dimensioned, and configured to envelope a food or beverage container 108. When the access door 103 is in an open state it provides access to the chamber 102 and when the access door 103 is in a closed state it blocks access to the chamber 102. The at least one UV light source 106 is configured to direct UV light at a predetermined intensity level and time duration onto a food or beverage container 108 positioned inside the chamber 102 in such a way as to result in sanitizing of surfaces of the food or beverage container 108. When the access door 103 is in the closed state a UV sanitation cycle is initiated using the UV light source 106 and when the UV sanitation cycle is complete, the access door 103 is moved to the open state.

In certain embodiments, the sanitizing system 100 is sized and dimensioned to fit on a counter or table top. In some such embodiments, the sanitizing system 100 is configured to be placed and operate on a service counter, or similar, at a food or beverage service location. As such, the sanitizing system has similar dimensions as other countertop devices such as toaster ovens or coffee makers. For example, the sanitizing system 100 may be about 12 inches tall by about 8 inches wide, by about 8 inches deep, or equivalent. In certain such deployments, at least one side of the sanitizing system 100 is accessible from a "customer side" of the counter—that is the side of the service counter that a customer interacts with while another side of the sanitizing system 100 is accessible from the "employee side" of the counter—that is the side of the service counter that a retail employee interacts with. In certain embodiments, this allows the sanitization system 100 to act as a pass-through for the transfer of a food or beverage container 108 from a customer to an employee without requiring handling of un-sanitized containers 108 by the employee. Conversely, the sanitizing system 100 can be reversed such that the customer is provided access to a sanitized container 108 on the "customer side" that has been sanitized as it passed thru and from the "employee side". Other sizes, dimensions, and configurations will be apparent to one skilled in the art given the benefit of this disclosure.

The example food or beverage container sanitizing system 100 depicted in the figures uses a beverage container for the description and figures merely for purposes of teaching how the invention can be specifically implemented. However, those of skill in the art will readily appreciate that other food or beverage containers can be implemented in the system 100 described herein with modification to some of the components for the specific size, shape, and configuration of the containers, such that the present invention is intended to be universally applicable and operable for a variety of different food or beverage container configurations and is not limited to the specific beverage container shown and described. It should also be appreciated that for purposes of efficiency, the figures provided herewith depicting a beverage container and corresponding system are fully applicable to all possible food or beverage containers and corresponding systems. For the avoidance of doubt, references to the container 108 and corresponding system 100 herein are transferable to other food or beverage containers, such as but not limited to, pizza boxes, Asian food takeout containers, donut boxes, pastry boxes, to-go restaurant food containers, carbonated beverage cups, coffee cups, iced coffee cups, tea cups, water bottles, hot chocolate cups, other disposable food or beverage containers, and the like, which are considered to all fall within the scope of the present inventive system.

In certain embodiments, the food or beverage container 108 the sanitizing system 100 is designed and configured to accommodate a reusable food or beverage container. There is a growing interest in moving away from single-use or disposable containers and replacing them with reusable containers. In contrast to a single use of disposable containers that are typically discarded after use, reusable food or beverage containers are designed to be used multiple times and be washed or otherwise sanitized between uses. However, single-use or disposable containers can still benefit from the sanitizing provided from the sanitizing system 100 of the present invention by preventing the unintentional transfer of any germs arising from the handling or storage of the food or beverage container 108.

Figures 1A, 1B:
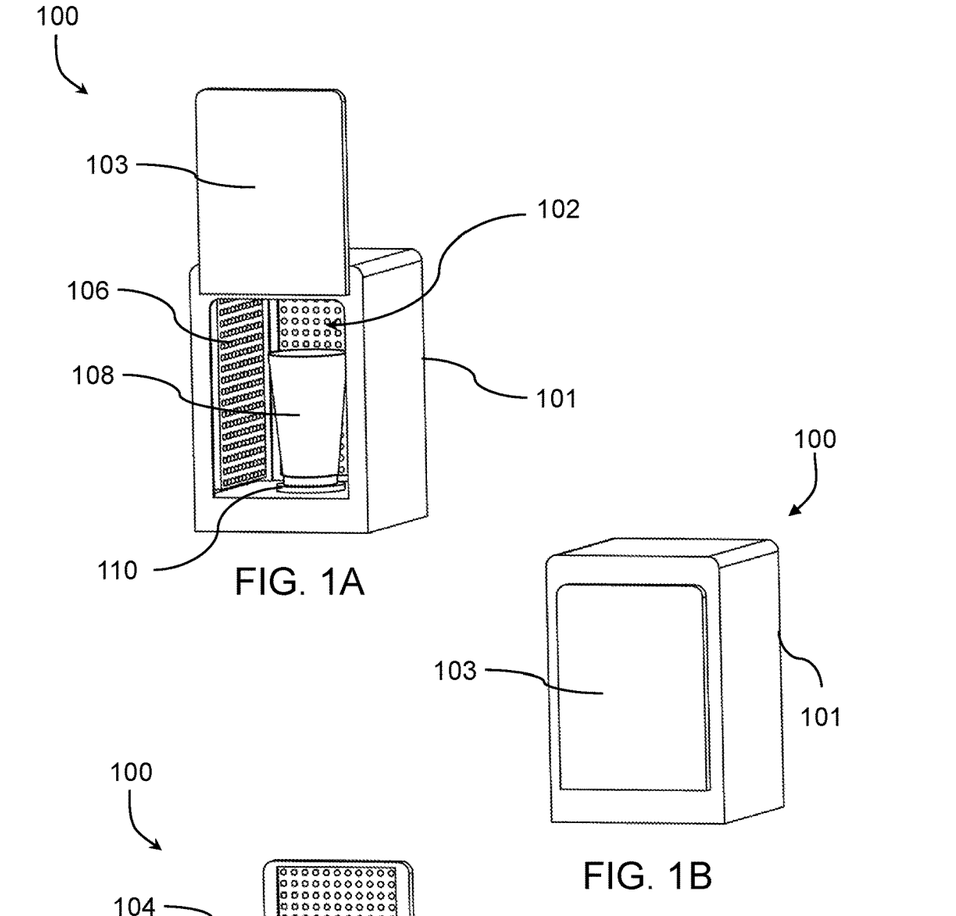
FIGS. 1A-1C are isometric views of a food or beverage container sanitizing system in accordance with embodiments of the present invention.
Figure 1C:
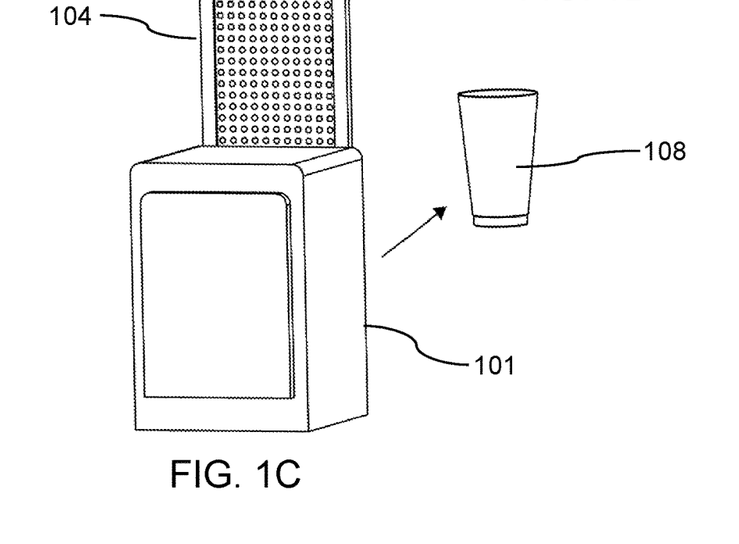

FIGS. 1A-1C depict one embodiment of a system 100 to sanitize the outer surface of a food or beverage container 108 (or any vessel) using UV-C (or other wavelengths) from at least one UV light source 106. In this embodiment, the system 100 is comprised of a housing 101 that has access to the chamber 102 from two sides; the entry ("dirty") side having an access door 103 and exit ("clean") side having a retrieval door 104. The system 100 is simple to use for both the customer and retail employee. The term "dirty" as utilized herein refers to a container that has not been sanitized or has been utilized or handled since a prior sanitizing. The term "clean" as utilized herein refers to a container that has received sanitizing processes utilizing the present invention and is deemed ready for use. In FIG. 1A, the customer places their food or beverage container 108 into the sanitizing system 100 from the "dirty" side via the access door 103 in an open position. In FIG. 1B the access door 103 is moved to a closed state and the food or beverage container 108 is sanitized within the enclosed chamber 102 during a UV sanitation cycle using at least one UV light source 106. In this embodiment, the at least one UV light source 106 is an array of UV lights disposed on one or more interior surfaces of the chamber 102. In FIG. 1C, after the UV sanitation cycle is complete, the retrieval door 104 is moved from a closed state to an open state allowing the retail employee to remove the sanitized container 108 on the "clean" side. In some embodiment of the invention, the food or beverage container 108 or UV light source 106 is rotated to evenly distribute UV light to the surface of the food or beverage container 108 to be sanitized. In this example, a rotating base 110 is provided to rotate the food or beverage container 108 within the chamber 102 providing more thorough exposure to the array of at least one UV light sources 106 on the inner surface of the chamber 102.

In some embodiments, the access door 103, as well as the retrieval door 104, to the chamber can be automated to open and close automatically to eliminate the need to touch anything but the food or beverage container 108 itself when using the system 100. In some embodiments, the automatic opening and closing of the door(s) makes it possible to have a single access door 103, such as on the top of the housing 101, for both entry and exit, without the risk of spreading germs. In some such embodiments an identification device, such as an RFID tag, bar-code, QR code, or the like on or embedded within the container 108 is read by a reader of the sanitizing system 100 and is used to unlock the access door 103 or retrieval door 104, automatically open the door 103, 104, or otherwise be used to initiate the sanitization cycle of the device. In still other embodiments, the opening or closing of the doors 103, 104 or the initiation of a sanitation cycle is actuated by a switch, button, motion sensor, or optical sensor. Whether manually or automatically closed, the access door 103, as well as the retrieval door 104, are locked during the sanitation cycle as a safety precaution to prevent inadvertent UV exposure to a user. Conversely, there may be an automatic shut-off of the one or more UV light sources 106 if the access door 103 or retrieval door 104 are opened before a sanitation cycle is complete.

Figures 2A, 2B, 2C:
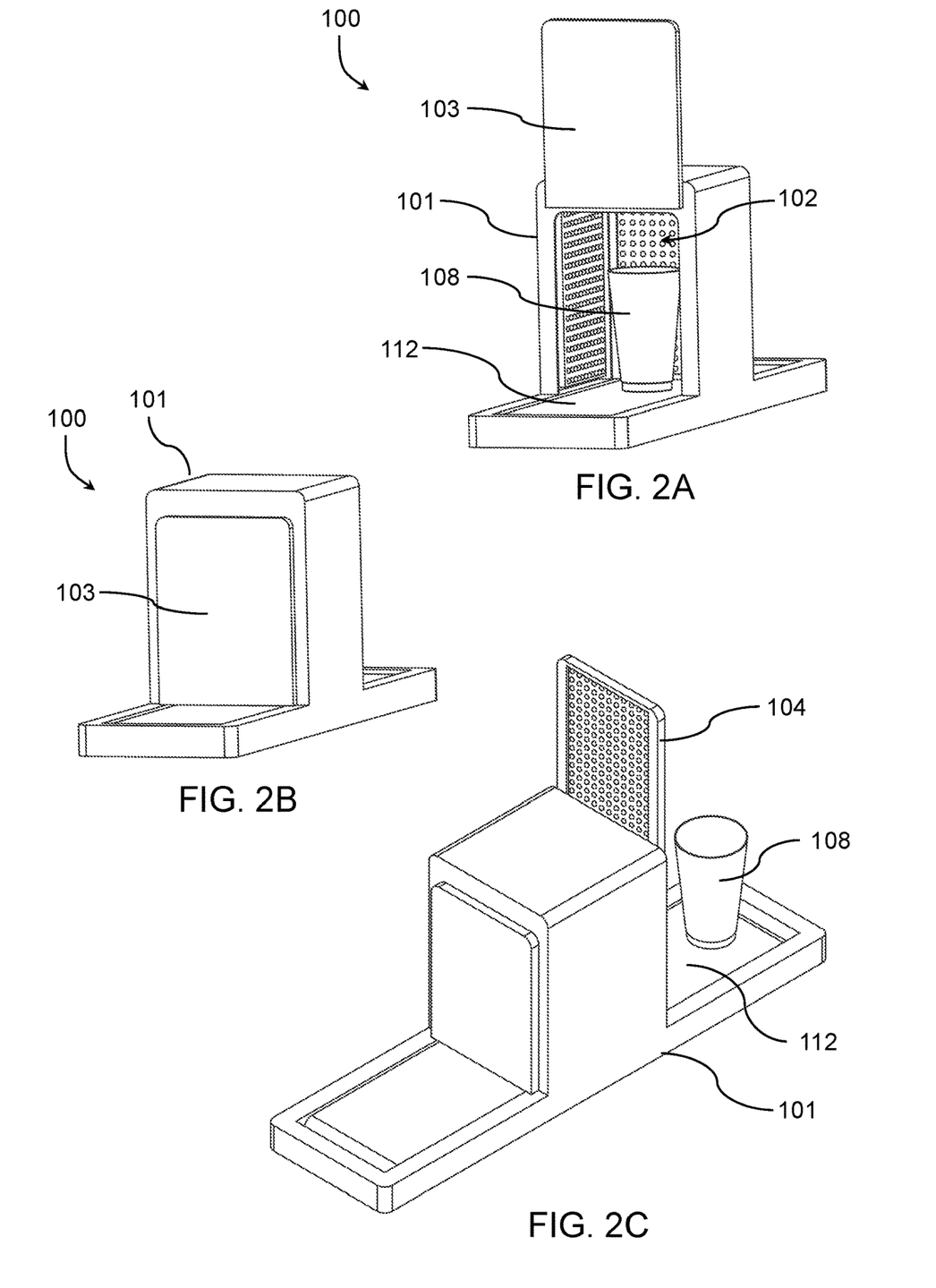
FIGS. 2A-2C are isometric views of a food or beverage container sanitizing system with conveyance in accordance with embodiments of the present invention.

FIGS. 2A-2C depict a system similar to FIGS. 1A-1C with the addition of a conveyor 112 to move the used food or beverage container 108 into the chamber 102 on the "dirty" side and then move the sanitized food or beverage container 108 out of the chamber 102 on the "clean" side. This simplifies the loading and unloading of the system 100, as well as adds the ability to queue additional food or beverage containers 108 to be sanitized. In FIG. 2A, the customer places their food or beverage container 108 onto the conveyor 112, in this case a conveyor belt. The conveyor 112 then moves the food or beverage containers 108 into the sanitizing system 100 from the "dirty" side via the access door 103 in an open position. In FIG. 2B the access door 103 is moved to a closed state and the food or beverage container 108 is sanitized within the enclosed chamber 102 during a UV sanitation cycle using at least one UV light source 106. In FIG. 1C, after the UV sanitation cycle is complete, the retrieval door 104 is moved from a closed state to an open state and the conveyor 112 moves the now sanitized food or beverage container 108 out of the chamber through the retrieval door 104 allowing the retail employee to remove the sanitized food or beverage container 108 from the conveyor 112 on the "clean" side.

Figure 3:
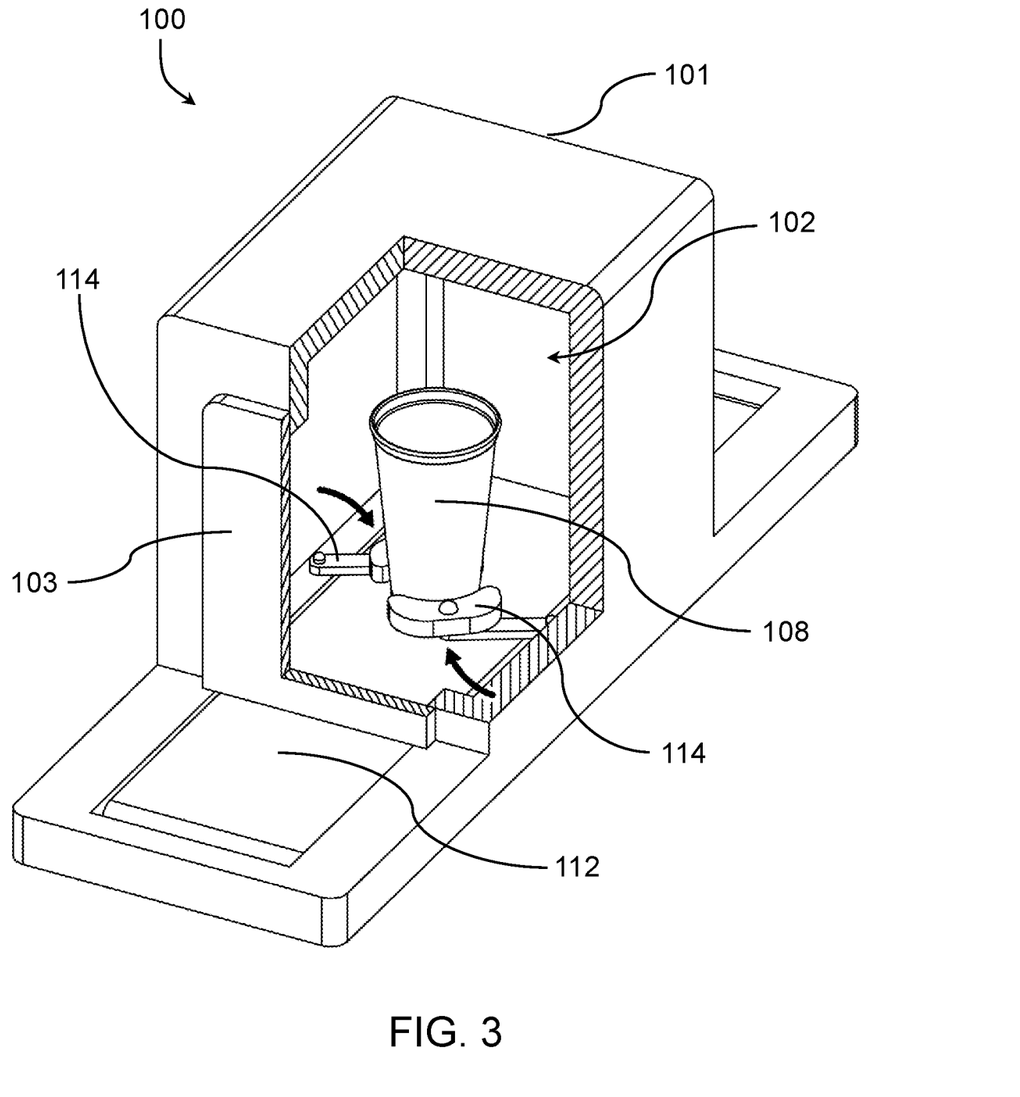
FIG. 3 is an isometric cut-away view of a food or beverage container sanitizing system with conveyance and a centering arm in accordance with embodiments of the present invention.

In some embodiments, container centering devices, such as the pivoting centering arms 114, shown in FIG. 3, are utilized to position the food or beverage container 108 in the center of the chamber 102 to ensure the even and expected distribution and strength of UV light on the surfaces.

The amount of UV radiation required to achieve a desired level of sanitation is referred to herein as a Dose (typically units: $mJ/cm^2$). The formula for a Dose can be expressed as the following: Dose=Intensity×Exposure Time. Wherein Intensity is the power per area of surface to be sanitized (typical unit: $mW/cm^2$) and the Exposure Time is the time that the surface is exposed to UV light (typical unit: seconds). Intensity is dependent on the particular UV light being used. For simplicity, the power of the light (in mW) can be used, although in reality, things like lens, coatings, age of light source will affect power of light. But for any UV light (no matter the power or other factors), the intensity is inversely proportional to the square of the distance to the surface (inverse square law function). As such, the closer the light is to the surface, the time required is greatly reduced. For example, at half (½) the original distance, the intensity is quadrupled (4X) so, required time is one quarter (¼) of the original time required. Similarly, if the distance is reduced by half again to a quarter (¼) of the original distance, the intensity is quadrupled again making it sixteen times (16×) more intense, and exposure time required is one sixteenth (1/16) of the original time required. As such, the time required to sanitize the food or beverage container 108 using UV light is minimized by moving the at least one light source 106 in close proximity to the outer surface. [

Figure 4A:
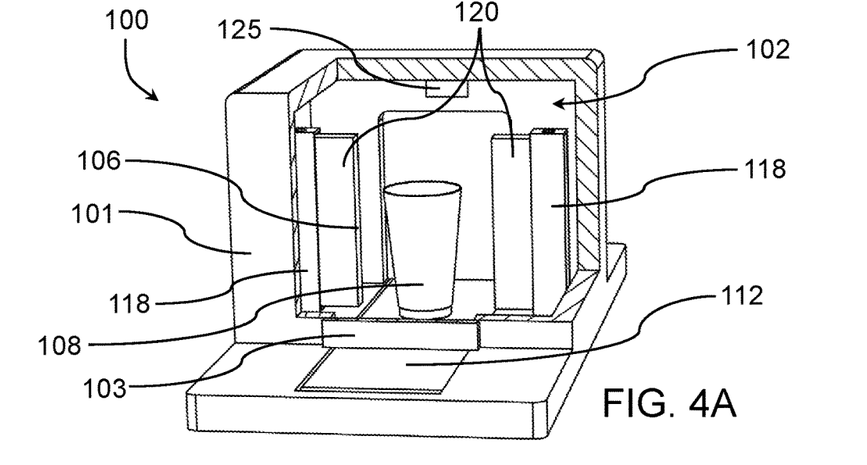
FIGS. 4A-4C are isometric cut-away views of a food or beverage container sanitizing system with a profiler in accordance with embodiments of the present invention.
Figure 4B:
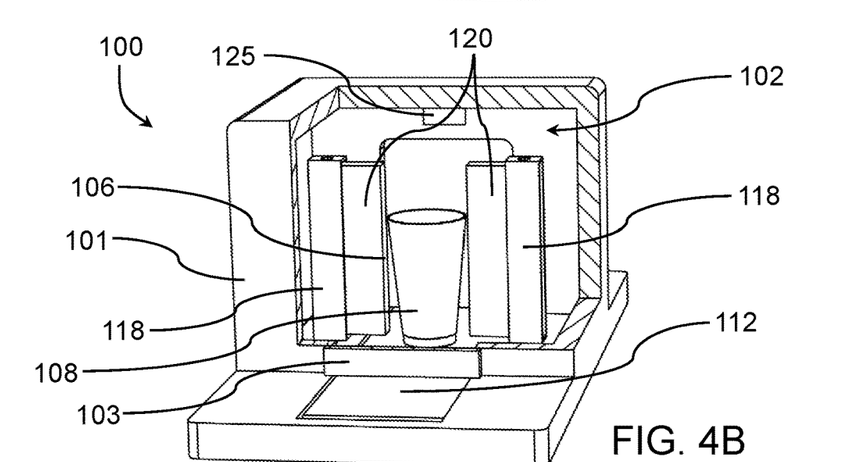
Figure 4C:
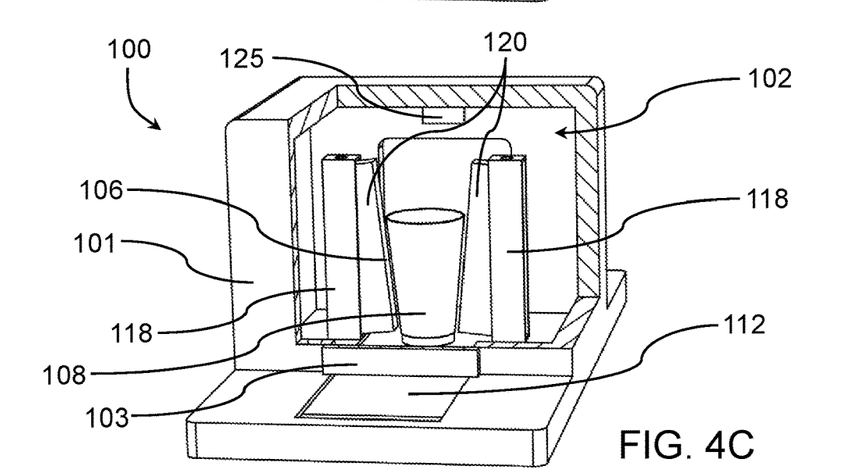

In one embodiment of the current invention shown in FIG. 4A-FIG. 4C, the at least one UV light source 106 is disposed on members 120 of a container profiler 118 that is able move the members 120 including the at least one UV light source 106 close to the outer surface of the food or beverage container 108 and, if required, adjust or otherwise conform to approximately match the tapered shape of commonly used food or beverage containers 108. In FIG. 4A, the profiler 118 is set at a starting position before being positioned to conform to the food or beverage container 108. In the embodiment of FIG. 4B, the profiler 118 has been adjusted to linearly move the members 120 in proximity to the outer surface of a food or beverage container 108. In certain embodiments, such as seen in FIG. 4C, the members 120 are further capable of moving angularly or otherwise pivoting or tilting to better conform to the profile of the food or beverage container 108.

It should be noted that any of the embodiments described herein can be alternatively embodied in fixed form. Specifically, and for example, looking at the embodiment depicted in FIG. 4C, this embodiment shows the members 120 angularly positioned to match the angle and profile of the food or beverage container 108. In the instance where the food or beverage container 108 will be the same shape in every instance of use, the members 102 can be permanently affixed to a shape and/or angle that matches the shape and profile of the food or beverage container and resemble the device as shown in this figure. In such an embodiment, the members 120 move around the food or beverage container 108 in fixed position, or the food or beverage container 108 can be rotated if the members 120 are fixed, resulting in the full application of UV light to the food or beverage container 108 to achieve the stated desired result. This alternative embodiment of fixed members 120 is anticipated herein for all operable embodiments, and all figures provided herein can be alternatively interpreted to show a fixed profile embodiment.

Figure 5A:
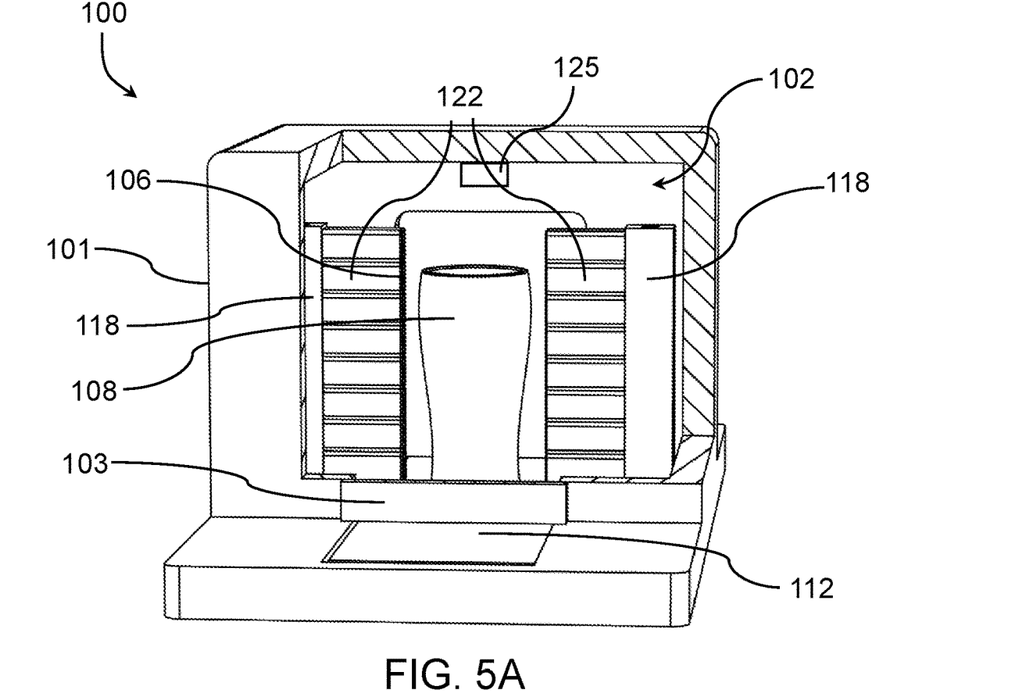
FIGS. 5A-5B are isometric cut-away views of a food or beverage container sanitizing system with a profiler having multiple linear moving members in accordance with embodiments of the present invention.
Figure 5B:
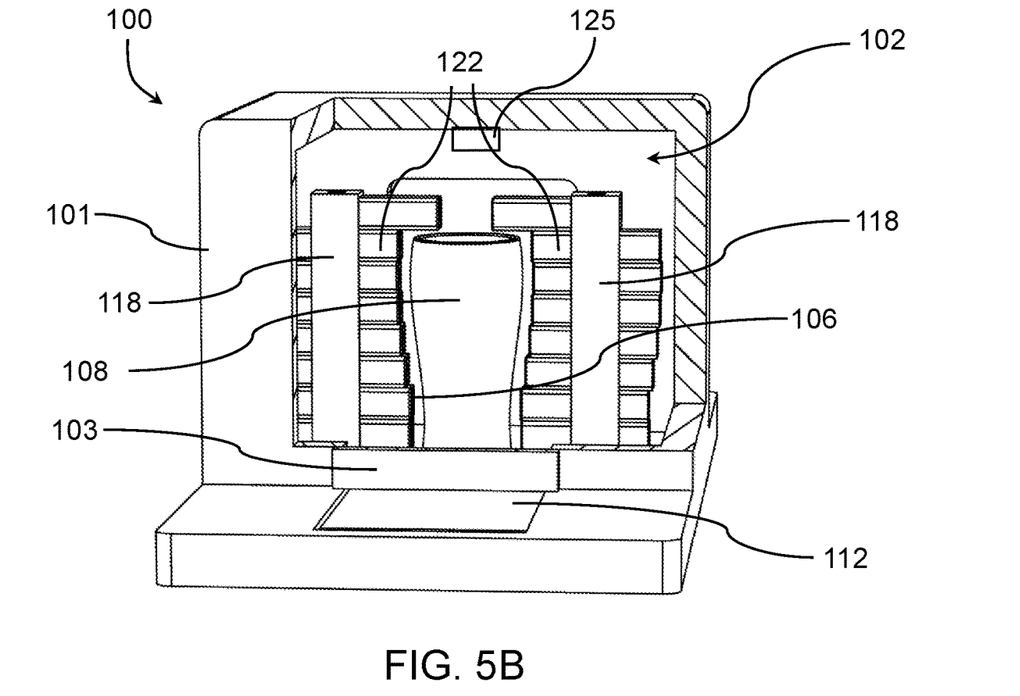
Figure 6:
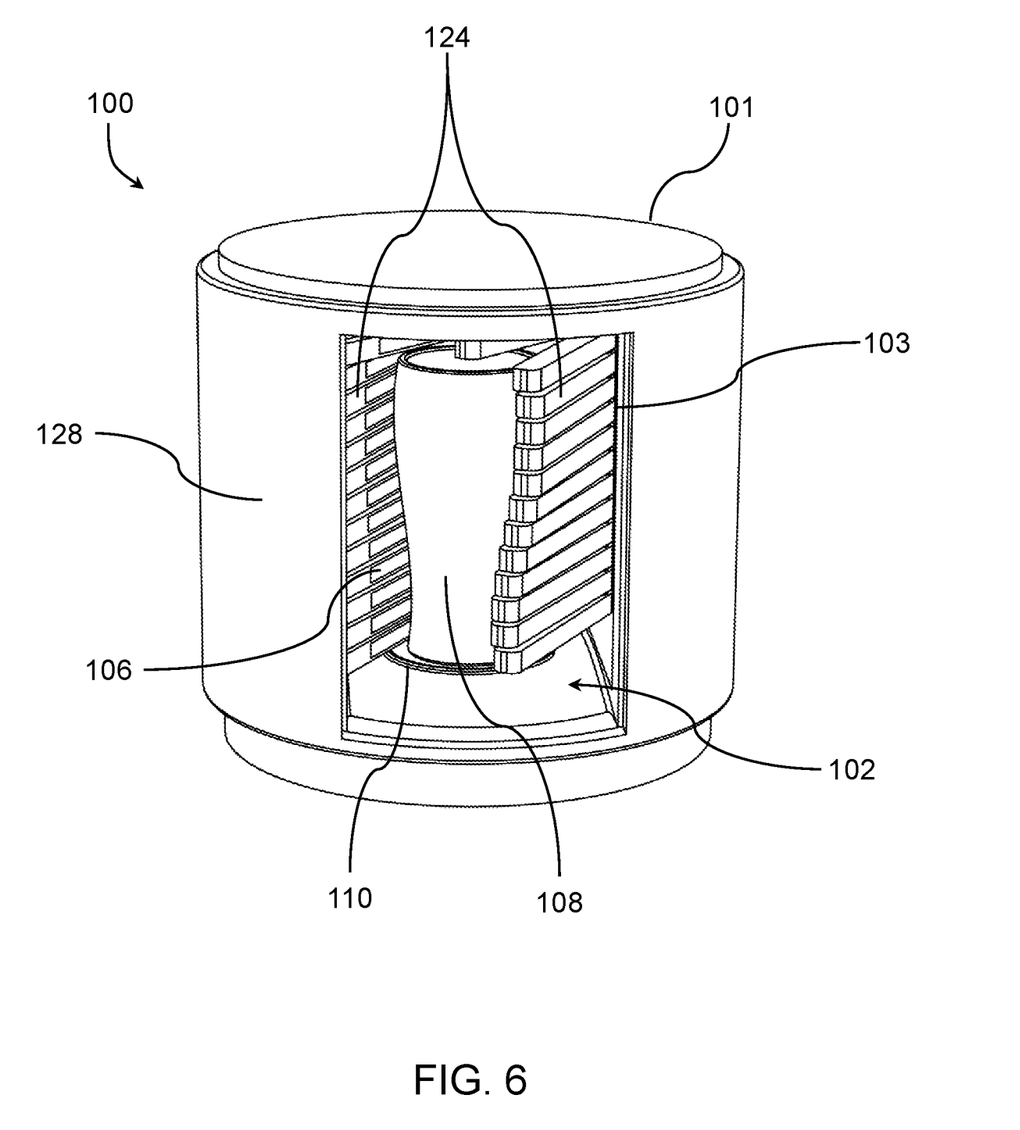
FIG. 6 is an isometric view of a food or beverage container sanitizing system with a revolving housing and a profiler having multiple articulating members in accordance with embodiments of the present invention.

In accordance with example embodiments, the UV light source(s) 106 of the profiler 118 are mounted to multiple movable profiling members 122 which can more accurately adjust to a variety of container profiles, such as the linear motion profiling members 122 shown in FIG. 5A and FIG. 5B and the pivoting profiling members 124 shown in FIG. 6. The positioning of the profiling members 120, 122, 124 of the profiler 118 close to the surface of the food or beverage container 108 can be achieved using one or more sensors such as a vision system 125, proximity sensors, or stall sensors incorporated into the profiler 118 used to detect when the profiling arms contact the surface, then back off slightly. In all embodiments, either the food or beverage container 108 or UV light source(s) 106 can be rotated, for example with a rotating base 110 as shown in FIG. 6, to ensure all surfaces are evenly sanitized without requiring additional time or an excessive number of UV light sources 106.

In accordance with example embodiments, such as seen in FIG. 6, the housing 101 or a sliding member 128 of the housing 101 providing the access door 103 can be rotated or revolved around the chamber 102 to move the access door 103 between an open state providing access to the chamber 102 or a closed state blocking access to the chamber 102.

As an alternative to moving the UV light source(s) 106 in close proximity to the food or beverage container 108, the food or beverage container 108 can be moved to close proximity to the UV light source(s) 106 in order to accomplish the same goal of minimizing the distance from the UV light source to the surface to be sanitized, and thus minimizing the time to sanitize.

Figure 7:
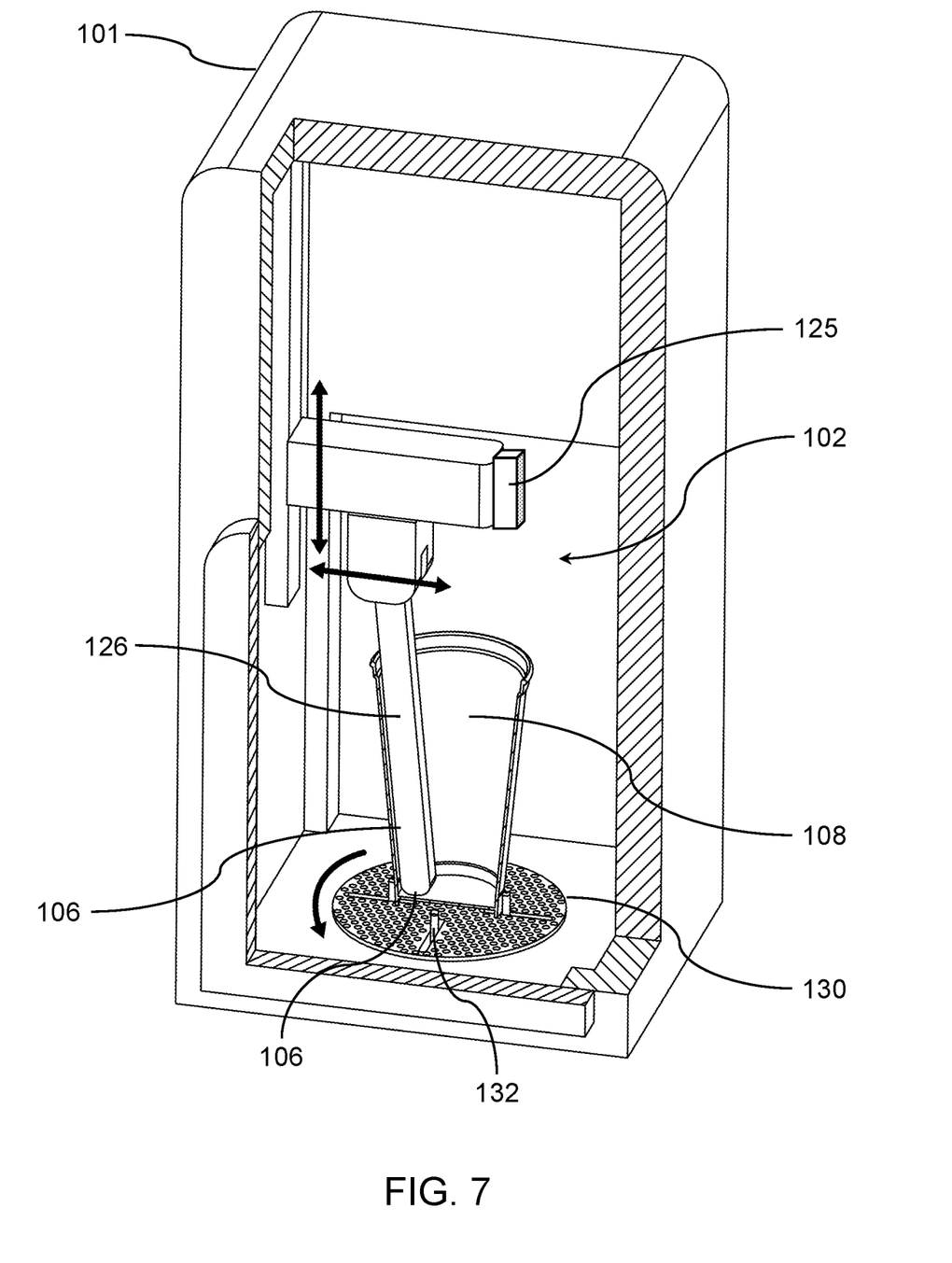
FIG. 7 is an isometric cut-away view of a food or beverage container sanitizing system with a rotating base and the UV light source disposed on an arm that extends into the interior volume of a container in accordance with embodiments of the present invention.

Since the outer surface of the food or beverage container 108 is what is handled by users, thus the surface most likely to transfer germs, it may be acceptable to only sanitize that surface. Alternatively, it may be desirable to sanitize all surfaces. An illustrative embodiment as shown in FIG. 7 uses a profiling arm 126 containing an array of at least one UV light sources 106, which is lowered into the food or beverage container 108 and adjusted to position the array of at least one UV light sources 106 in close proximity to the interior surface. A centering device, such as the centering fingers 132 on the perforated rotating base 130 of FIG. 7, or pivoting centering arms 114 as previously shown in FIG. 3, or any similar device, is used to properly position the food or beverage container 108 such that when rotated on the rotating perforated base 130, the profiling arm 126 maintains a position in close proximity to the surface to ensure proper sanitizing. Positioning of the profiling arm can be performed with the use of one or more sensors, such as vision system 125, proximity sensors, or stall sensors incorporated into the profiling arm 126. The array of at least one UV light sources 106 of the interior profiling arm 126 includes UV lights positioned to emit light down onto the interior bottom surface of the cup such that all interior surfaces are sanitized. To sanitize the bottom exterior of the cup, a UV light or UV light array (not shown) may be placed below a perforated base, in this case the perforated rotating base 130 as shown in FIG. 7. The positioning of at least one UV light source 106 below the base 130 and/or movement of the base 130 allows the emitted light to reach all areas of the bottom surface to ensure proper sanitization. It should be noted that any combination of the presented concepts may be combined to achieve a desired level of sanitization of the food or beverage container 108.

Alternately, in certain embodiments where a standardized food or beverage container 108 is used, the profiler 118 (including members 120, 122, 124), profiler arm 126, or the chamber 102 itself can have a fixed shape or configuration that conforms to the dimensions of the standardized container 108, such that the one or more UV light sources 106 are in close proximity to the surface(s) of the standardized container 108. This would simplify the system 100 as the profiler 118 would not require one or more sensors such as a vision system 125, proximity sensors, or stall sensors incorporated into the profiler 118 used to detect when the profiling arms contact the surface, then back off slightly.

In still other embodiments, where the food or beverage container 108 is provided with an identification device, such as radio frequency identification (RFID) tag, bar-code, QR code, or the like, the identification device can be used to identify the container 108 including the type or shape of the container 108 such that the profiler can adjust to conform to the shape of the identified container 108 placing the one or more UV light sources in close proximity to the surface(s) of the container 108.

Figures 8A, 8B, 8C:
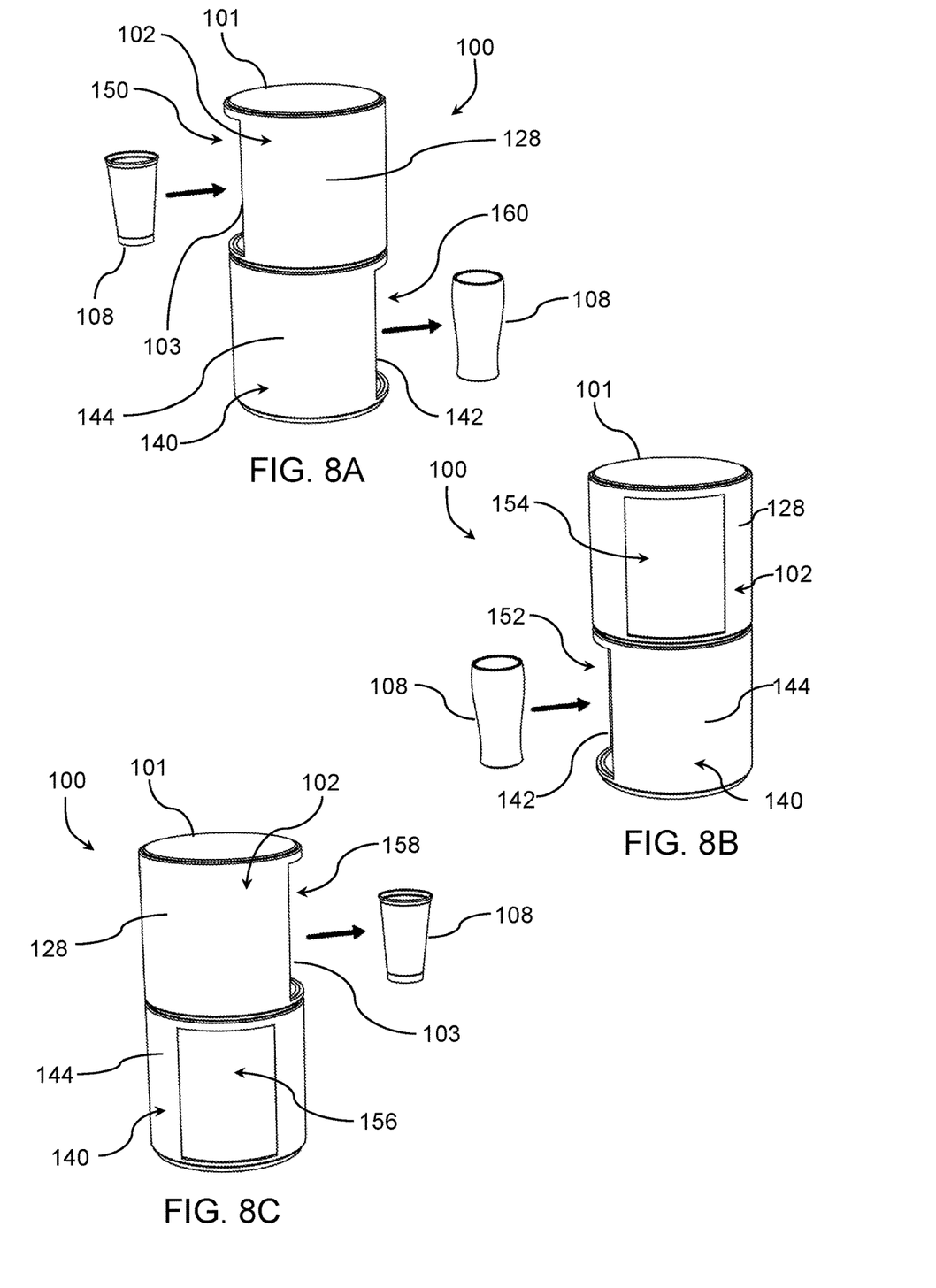
FIGS. 8A-8C are isometric views of a food or beverage container sanitizing system having two chambers and revolving housing in accordance with embodiments of the present invention.

Even when positioning the UV light source 106 in close proximity to the surface to be sanitized, the time required to achieve the appropriate level of sanitization may be too long when high through-put, or no waiting time to load, is desired. FIGS. 8A-8C show a dual stacked version of the revolving door system from FIG. 6. Here a second chamber 140 is provided that is sized, dimensioned, and configured to envelope a food or beverage container 108. A second access door 142 is provided on second sliding member 144. The second access door 142 provides access to the second chamber 140 when the second access door 142 is in an open state and blocks access to the second chamber 140 when the second access door 142 is in a closed state. At least one UV light source 106 (not shown in this figure) is disposed within the second chamber 140 and configured to direct UV light at a predetermined intensity level and time duration onto a food or beverage container 108 positioned inside the second chamber 140 in such a way as to result in sanitizing of surfaces of the food or beverage container 108. The housing 101, in this case, the first sliding member 128 and second sliding member 144 of the housing 101, rotate to expose the "dirty" side opening, the "clean" side opening, or a closed position with no openings for the sanitizing process to take place within the chambers 102, 140. In FIG. 8A the first sliding member 128 of the housing 101 is in a first position 150 where the first access door 103 is in an open state for receiving an un-sanitized food or beverage container 108. The second sliding member 144 is in a second position 160 where the second access door 142 is in an open state allowing for the removal of a sanitized food or beverage container 108 from the second chamber 140. In FIG. 8B the first sliding member 128 is moved such that the first access door 103 is in a closed state 154 during which a UV sanitization cycle is run. The second sliding member 144 is moved to a first position 152 where the second access door 142 is in an open state for receiving an un-sanitized food or beverage container 108. In FIG. 8C the first sliding member 128 is moved to a second position 158 where the first access door 103 is in an open state allowing for the removal of the now sanitized food or beverage container 108. The second sliding member 144 has been moved such the such that the second access door 142 is in a closed state 156 during which a UV sanitization cycle is run in the second chamber 140. The sliding members 128, 144 can then be moved back to the positions shown in FIG. 8A.

By having dual systems, such as the stacked systems as shown in FIGS. 8A-8C, or some other combination of 2 or more systems, the overall through-put of the system is increased and wait times to use a system are decreased as one system can be loaded or unloaded while the other is running the sanitization process. These systems can be individual stand-alone systems, or a single system containing multiple chambers.

In certain embodiments, one of the first chamber 102 or second chamber 140 may be arranged or otherwise configured such that it operates in the opposite direction from the other chamber. For example, the first position 150 of the sliding member 128 may provide access to the "clean" side of the first chamber 102 where a sanitized food or beverage container 108 can be retrieved and the second position 158 of the sliding member 128 provides access to the "dirty" side of the first chamber 102 where a un-sanitized container can inserted to be sanitized by the system 100. Alternately, the second position 160 of the second sliding member 144 may be on the "dirty" side of the second chamber 140 and the first position 152 of the second sliding member 144 may be on the "clean" side of the second chamber 140. Such configurations allow bi-directional sanitation where a food or beverage container 108 can be sanitized during both the transition of the food or beverage container 108 from the customer to employee and from the employee to the customer.

Figure 9:
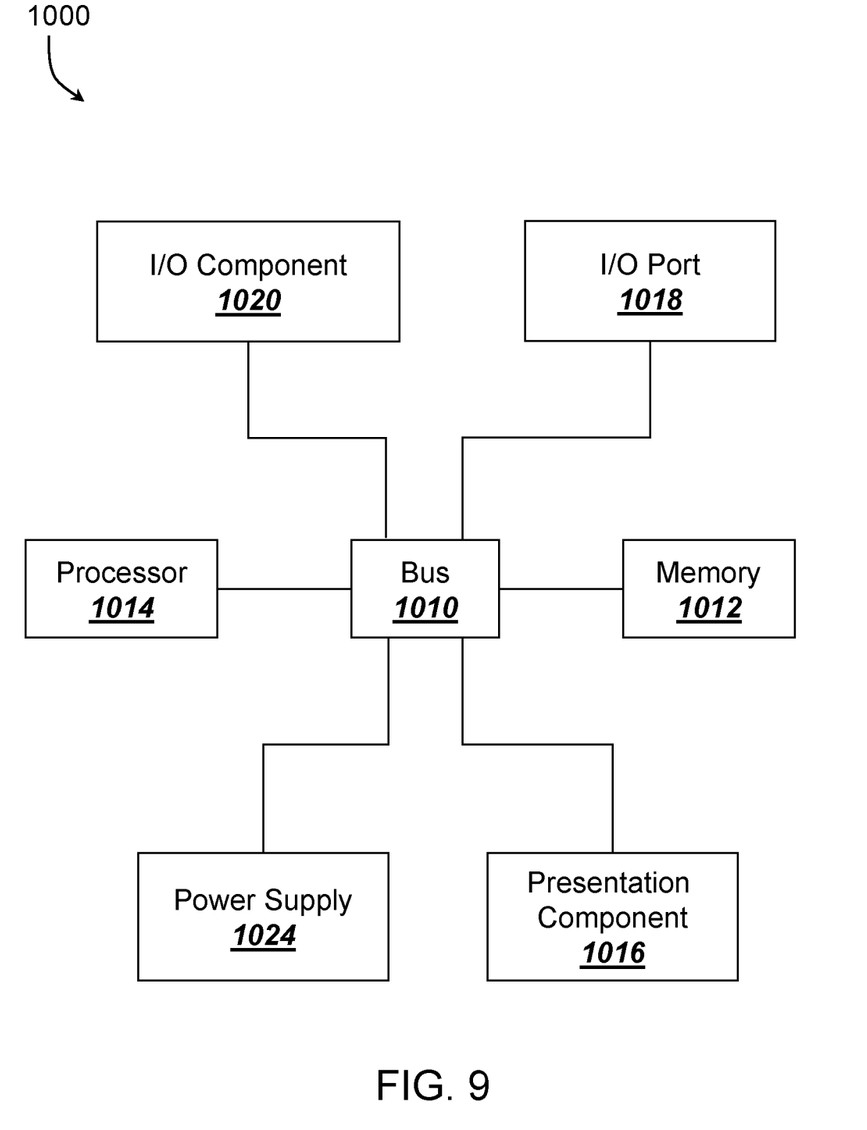
FIG. 9 a is a diagrammatic illustration of a computing device and related hardware for use in implementation of the present invention.

FIG. 9 depicts an example electronic, computer, or computing device 1000 that can be used to implement one or more aspects of the present invention, including control systems for managing the scanning, sensing, automating and similar functions described herein. The functionality and hardware of such computing device 1000 may be implemented in any of the electronic hardware systems or subsystems described herein as involving or using a "computer" or "computing device" or the like, or related hardware for providing all or part of the described functionality, provided as a separate device or integrated into a system or subsystem described herein, as would be appreciated and understood by those of skill in the art. The terms "computer", "computing device", and the like utilized herein are intended to mean a processor at its most basic form, on up to more complex computing systems, including servers and cloud-based systems, in accordance with conventional meanings of such terms. However, for purpose of completeness, example components and related accessories that are intended to be encompassed by the use of the terms "computer", "computing device", "processor", and the like will be provided below in example nonlimiting form.

The computing device 1000 is merely an illustrative example of a suitable computing environment and in no way limits the scope of the present invention. An "electronic device", "remote device," or "personal electronic device" as represented in figures and description herein, can include a "workstation," a "server," a "laptop," a "desktop," a "handheld device," a "mobile device," a "tablet computer," a "processor," or other computing devices, as would be understood by those of skill in the art. Given that the computing device 1000 is depicted for illustrative purposes, embodiments of the present invention may utilize any number of computing devices 1000 in any number of different ways to implement a single embodiment of the present invention. Accordingly, embodiments of the present invention are not limited to a single computing device 1000, as would be appreciated by one with skill in the art, nor are they limited to a single type of implementation or configuration of the example computing device 1000.

The computing device 1000 can include a bus 1010 that can be coupled to one or more of the following illustrative components, directly or indirectly: a memory 1012, one or more processors 1014, one or more presentation components 1016, input/output ports 1018, input/output components 1020, and a power supply 1024. One of skill in the art will appreciate that the bus 1010 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, the figures herein are merely illustrative of an exemplary computing device 1000 that can be used to implement one or more embodiments of the present invention, and in no way limits the invention.

The computing device 1000 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 1000.

The memory 1012 can include computer-storage media in the form of volatile and/or nonvolatile memory. The memory 1012 may be removable, non-removable, or any combination thereof. Exemplary hardware devices are devices such as hard drives, solid-state memory, optical-disc drives, and the like. The computing device 1000 can include one or more processors that read data from components such as the memory 1012, the various I/O components 1020, etc. Presentation component(s) 1016 present data indications to a user or other device. Exemplary presentation components include a display device, speaker, printing component, vibrating component, etc.

The I/O ports 1018 can enable the computing or electronic device 1000 to be logically coupled to other devices, such as I/O components 1020. Some of the I/O components 1020 can be built into the computing device 1000. Examples of such I/O components 1020 include a sensor (including but not limited to: weight sensor, infrared sensor, camera, chemical sensor, microphone, or the like), keypad, touchpad, joystick, recording or storage device, game pad, satellite dish, scanner, printer, wireless device, networking device, and the like, as appropriate.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A food or beverage container sanitizing system, comprising:
   a housing;
   a chamber inside the housing having a top, one or more sides, and a bottom, the chamber being sized, dimensioned, and configured to envelope a food or beverage container;
   an access door providing access to the chamber when the access door is in an open state and blocking access to the chamber when the access door is in a closed state;
   a rotating base for rotating the food or beverage container within the chamber; and
   at least one UV light source disposed on an inner surface of the one or more sides of the chamber and configured to direct UV light at a predetermined intensity level and time duration onto a food or beverage container positioned inside the chamber in such a way as to result in sanitizing of surfaces of the food or beverage container;
   wherein when the access door is in the closed state a UV sanitation cycle is initiated using the UV light source and when the UV sanitation cycle is complete, the access door is moved to the open state; and wherein the housing rotates around the chamber and wherein the access door connected to the housing receives un-sanitized food or beverage container in a first position located on a first side of the chamber and rotates to a second position located on second side of the chamber to provide access to a sanitized food or beverage container.

2. The sanitizing system of claim 1, wherein the food or beverage container the system is configured to sanitize a reusable food or beverage container.

3. The sanitizing system of claim 1, further comprising a retrieval door opposite the access door, the retrieval door providing access to the chamber when the retrieval door is in an open state and blocking access to the chamber when the retrieval door is in a closed state.

4. The sanitizing system of claim 3, wherein the access door is configured to receive an un-sanitized food or beverage container and the retrieval door is configured to allow retrieval of a sanitized food or beverage container after the UV sanitation cycle.

5. The sanitizing system of claim 1, further comprising a container centering device disposed within the chamber.

6. The sanitizing system of claim 5, wherein the food or beverage container centering device comprises at least one mechanical arm.

7. The sanitizing system of claim 1, wherein the at least one UV light source comprises an array of UV lights.

8. The sanitizing system of claim 1, wherein the at least one UV light source is disposed on an arm that extends into an internal volume of the food or beverage container to sanitize an interior surface of the container.

9. The sanitizing system of claim 8, wherein the arm is configured to place the UV light source in proximity to the interior surface of the container allowing for effective sanitation at a lower intensity level or time duration.

10. The sanitizing system of claim 8 wherein the arm is configured to rotate within the internal volume of the container to distribute application of UV light.

11. The sanitizing system of claim 1, further comprising:
a second chamber inside the housing that is sized, dimensioned, and configured to envelope the food or beverage container;
a second access door providing access to the second chamber when the second access door is in an open state, and blocking access to the second chamber when the second access door is in a closed state; and
at least one UV light source disposed within the second chamber and configured to direct UV light at a predetermined intensity level and time duration onto the food or beverage container positioned inside the second chamber in such a way as to result in sanitizing of surfaces of the food or beverage container;
wherein when the second access door is in the closed state a UV sanitation cycle is initiated using the UV light source and when the UV sanitation cycle is complete, the second access door is moved to the open state.

12. The sanitizing system of claim 11, wherein the second chamber is configured to operate in an opposite direction of the chamber.

13. The sanitizing system of claim 1, wherein the access door is locked during the sanitation cycle and unlocked after the sanitation cycle.

14. The sanitizing system of claim 1, wherein the access door automatically transitions between the closed and open states.

15. A method for sanitizing a food or beverage container, the method comprising:
providing a food or beverage container sanitizing system, comprising:
a housing;
a chamber inside the housing having a top, one or more sides, and a bottom, the chamber being sized, dimensioned, and configured to envelope a food or beverage container;
an access door providing access to the chamber when the access door is in an open state and blocking access to the chamber when the access door is in a closed state;
a rotating base for rotating the food or beverage container within the chamber;
at least one UV light source disposed on an inner surface of one or more sides of the chamber and configured to direct UV light at a predetermined intensity level and time duration onto a food or beverage container positioned inside the chamber in such a way as to result in sanitizing of surfaces of the food or beverage container;
wherein when the access door is in the closed state a UV sanitation cycle is initiated using the UV light source and when the UV sanitation cycle is complete, the access door is moved to the open state; and
wherein the housing rotates around the chamber and wherein the access door connected to the housing receives un-sanitized food or beverage container in a first position located on a first side of the chamber and rotates to a second position located on second side of the chamber to provide access to a sanitized food or beverage container;
inserting an un-sanitized food or beverage container into the chamber;
initiating a UV sanitation cycle sanitizing the food or beverage container; and
retrieving a now sanitized food or beverage container from the chamber.

* * * * *